US00PP36815P2

(12) United States Plant Patent
Holtmaat

(10) Patent No.: US PP36,815 P2
(45) Date of Patent: Jul. 8, 2025

(54) ***RUDBECKIA* PLANT NAMED 'RUDBDIV658'**

(50) Latin Name: *Rudbeckia hirta*
Varietal Denomination: RUDBDIV658

(71) Applicant: Henricus Maria Joseph Holtmaat, Zuidwolde (NL)

(72) Inventor: Henricus Maria Joseph Holtmaat, Zuidwolde (NL)

(73) Assignee: NOVA PERENNE BV, Zuidwolde (NL)

( * ) Notice: Subject to any disclaimer, the term of this patent is extended or adjusted under 35 U.S.C. 154(b) by 0 days.

(21) Appl. No.: 19/037,027

(22) Filed: Jan. 24, 2025

(30) Foreign Application Priority Data

Jul. 31, 2024 (QZ) ..... PBR 20241793

(51) Int. Cl.
*A01H 5/02* (2018.01)
*A01H 6/14* (2018.01)

(52) U.S. Cl.
USPC ..... Plt./474
CPC ..... *A01H 6/14* (2018.05)

(58) Field of Classification Search
USPC ..... Plt./474
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Rudbeckia* plant named 'RUDBDIV658' that is characterized by its short plant height, its compact plant habit, its flowering that commences early in the season, and its inflorescences with solid yellow ray florets.

2 Drawing Sheets

Botanical classification: *Rudbeckia hirta.*
Variety denomination: 'RUDBDIV658'.

CROSS-REFERENCE TO RELATED APPLICATIONS

This application claims priority to European Community Plant Variety Office (CPVO) Plant Breeder's Rights Application No. 2024/1793 filed on Jul. 31, 2024, under 35 U.S.C. 119(f), the entire contents of which is incorporated by reference herein. The Applicant received the information for the Plant breeders' rights application directly from the Inventor. This application is also co-pending with U.S. Plant Patent Applications filed for plants derived from the same breeding program that are entitled *Rudbeckia* Plant Named 'RUDBCHR650' (U.S. Plant patent application Ser. No. 19/037,008), *Rudbeckia* Plant Named 'RUDBSUN303' (U.S. Plant patent application Ser. No. 19/037,040).

BACKGROUND OF THE INVENTION

The present invention relates to a new and distinct cultivar of *Rudbeckia hirta* and will hereafter by referred to by its cultivar name, 'RUDBDIV658'. The new cultivar is an herbaceous perennial grown for use as a landscape plant.

'RUDBDIV658' was selected in July of 2019 by the Inventor from amongst seedlings in a trial field in Zuidwolde, Netherlands that had been planted with seed derived from open pollination of numerous unpatented and unnamed proprietary plants from the Inventor's breeding program. The exact parentage is therefore unknown.

Asexual propagation of the new cultivar was first accomplished under the direction of the Inventor by tissue culture using meristematic tissue in Heerhugowaard, The Netherlands in December of 2021. Asexual propagation by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'RUDBDIV658' as a unique cultivar of *Rudbeckia.*

1. 'RUDBDIV658' exhibits a short plant height.
2. 'RUDBDIV658' exhibits a compact plant habit.
3. 'RUDBDIV658' exhibits flowering that commences early in the season.
4. 'RUDBDIV658' exhibits inflorescences with solid yellow ray florets.

'RUDBDIV658' can be compared to the *Rudbeckia* cultivars 'RUDHT53' (U.S. Plant Pat. No. 30,727) and 'RUDHT37' (U.S. Plant Pat. No. 30,657). 'RUDHT53' and 'RUDHT37' are both similar to 'RUDBDIV658' in inflorescence coloration. 'RUDHT53' differs from 'RUDBDIV658' in having an overall weaker plant habit that dies off earlier in the season, inflorescences with ray florets that are darker yellow in color that fade to a lighter yellow at the distal end, and in commencing bloom later in the season. 'RUDHT37' differs from 'RUDBDIV658' in having a taller plant height, inflorescences that are larger in size, and in commencing bloom later in the season.

'RUDBDIV658' can also be compared to the co-pending cultivars of *Rudbeckia*; 'RUDBCHR650' and 'RUDBSUN303'. Both are similar to 'RUDBDIV658' in having short plant heights and in commencing bloom early in the season. 'RUDBCHR650' differs from 'RUDBDIV658' in having inflorescences that are slightly larger in size and ray florets that fade to a lighter yellow at the tips. 'RUDBSUN303' differs from 'RUDBDIV658' in having bi-color ray florets.

BRIEF DESCRIPTION OF THE DRAWINGS

The accompanying color photographs illustrate the overall appearance and distinct characteristics of the new *Rudbeckia*. The photographs were taken of a 3-month-old plant of 'RUDBDIV658' as grown outdoors in a 17-cm container in Zuidwolde, The Netherlands.

The photograph in FIG. 1 is a side view of 'RUDBDIV658' in bloom.

Figure 1:
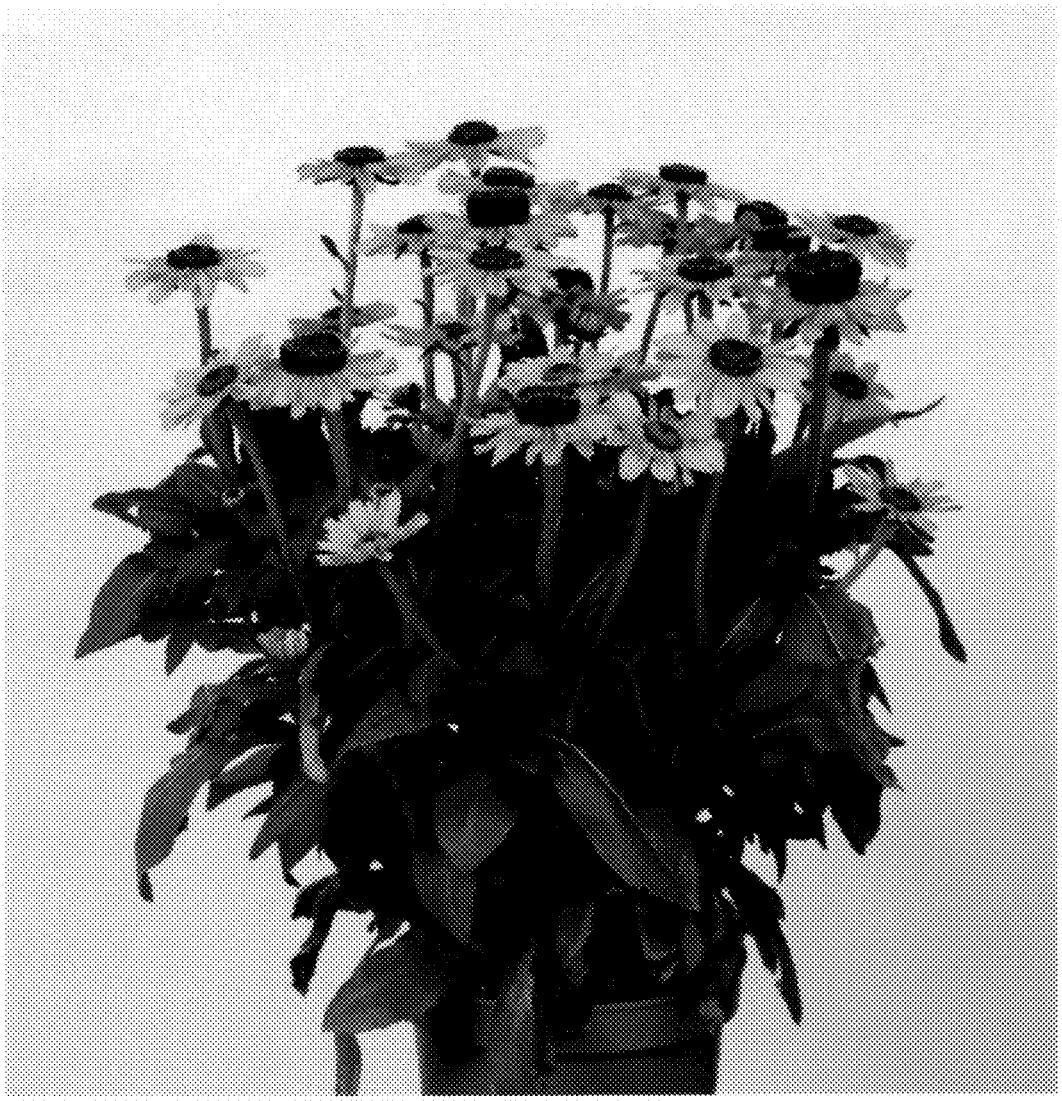
Figure 2:
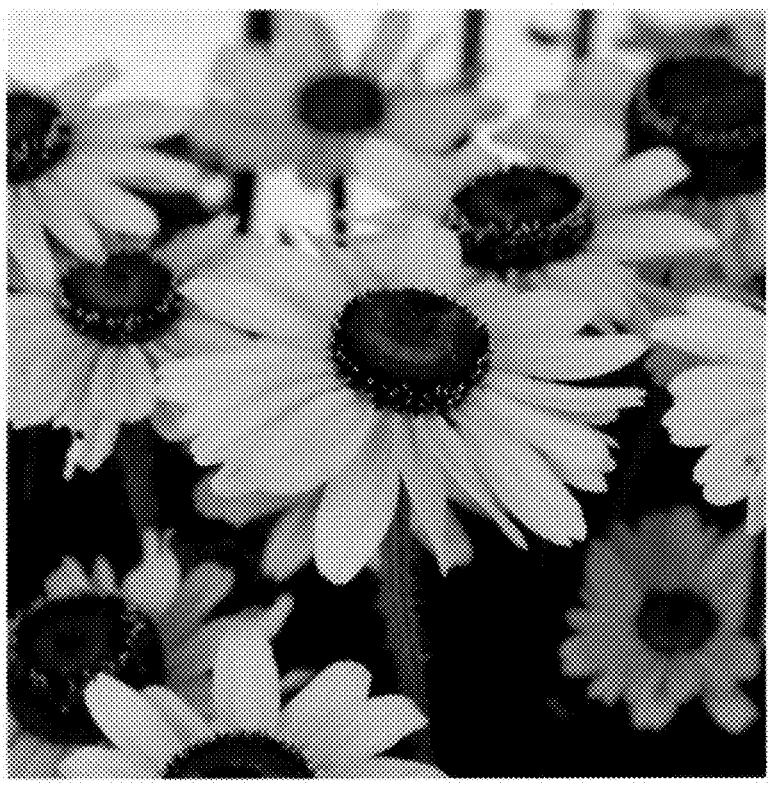

The photograph in FIG. 2 provides a close-up view of an inflorescence of 'RUDBDIV658'.

Figure 3:
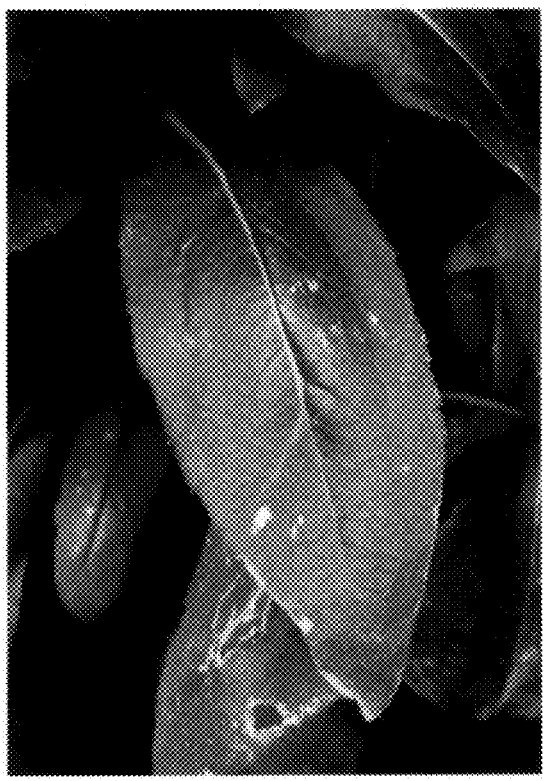

The photograph in FIG. 3 provides a close-up view of the foliage of 'RUDBDIV658'.

The colors in the photographs are as close as possible with the photographic and printing technology utilized and the color values cited in the detailed botanical description accurately describe the colors of the new *Rudbeckia*.

BOTANICAL DESCRIPTION OF THE PLANT

The following is a detailed description of 3-month-old plants of 'RUDBDIV658' as grown outdoors in 17-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—June to July in The Netherlands.

*Plant type*.—Perennial.

*Plant habit*.—Broadly upright, compact.

*Plant shape*.—Obovate.

*Height and spread*.—Average of 37 cm in height from soil level to top of foliar plane and 46 cm in height from soil level to top of floral plane, 45 cm in diameter as a 3-month old plant grown in a container.

*Hardiness*.—At least in U.S.D.A. Zones 4 to 10.

*Diseases and pests*.—No susceptibility or resistance to diseases or pests has been observed.

*Root description*.—Fine and fibrous.

*Propagation*.—Tissue culture.

*Root development*.—An average of 2 weeks for root initiation with a young rooted plant produced in an average of 4 weeks.

*Growth rate and vigor*.—Moderate vigorous.

Stem description:

*Shape*.—Moderately angled, 5-sided.

*Stem color*.—Young stems; 144B, mature stems; 144A, tinged with 187C, moderately ridged; 146D.

*Stem size*.—An average of 6.5 mm in diameter and an average of 17.7 cm in length.

*Stem surface*.—Moderately glossy and densely covered with strigose hairs an average of 2 mm in length and N155A in color.

*Stem number*.—Average of 13 main stems, 5 lateral branches per main stem.

*Internode length*.—An average of 3 cm in length.

*Stem aspect*.—Main stems; average of 22.5° to vertical, lateral branches; average of 15° to main stems.

*Branching*.—Freely branching from base with lateral stems.

Foliage description:

*Leaf shape*.—Narrow obovate to oblanceolate.

*Leaf division*.—Simple.

*Leaf base*.—Long cuneate.

*Leaf apex*.—Acute.

*Leaf venation*.—Pinnate, color upper surface 137A, color lower surface 138A.

*Leaf margins*.—Coarsely shallowly crenate-serrate, coarsely slightly undulate.

*Leaf attachment*.—Petiolate.

*Leaf arrangement*.—Alternate.

*Leaf size*.—Average of 15.4 cm in length and 5.2 cm in width.

*Leaf color*.—Young upper surface; 137A, young lower surface; 138A, mature upper surface; NN137A to NN137B, mature lower surface; 147B.

*Leaf surface*.—Upper surface very slightly glossy, lower surface slightly glossy, both surfaces rough to the touch, densely pubescent with short strigose hairs; an average of 2 mm in length and 156D in color.

*Petioles*.—Average of 5.5 mm in length, strong, flattened, average diameter at widest point 1 cm and at narrowest point 4 mm, upper surface color; 145A to 145B, lower surface color; 145A, both surfaces slightly glossy and densely covered with strigose hairs; an average of 1.5 mm in length and 156D in color.

Flower description:

*Type*.—Terminal capitulum, consisting of ray florets and disc florets.

*Capitulum number*.—5 per stem, up to 65 per plant.

*Lastingness of inflorescence*.—Average of 2 weeks, persistent.

*Capitulum size*.—Matures to about 3.1 cm in height and 8.1 cm in diameter, disc size is an average of 2.9 cm in diameter.

*Fragrance*.—None.

*Involucral bracts* (*phyllaries*).—Cuneate base, obtuse apex, narrow oblanceolate to narrow oblong in shape, entire margins, average of 32 arranged in 3 rows, rotate, slightly curved upward, 2.4 cm in length and 8 mm in width, color; upper surface when fully open 137A, margins NN137A, lower surface when fully open 138A to 138B, both surfaces slightly glossy and densely covered with strigose hairs; an average of 2 mm in length and NN155D in color, margins are moderately to densely covered with strigose hairs; 1.5 mm in length and 156D in color.

*Receptacle*.—Broad ovate in shape, an average of 1.3 cm in height and diameter, 157B in color.

*Buds*.—Shape; broad ovate, immature ray florets pointed upward and slightly curled inwards, 1.8 cm in length, width; excluding involucral bracts 1.9 cm, including involucral bracts 3 cm, surfaces are matte and densely covered with strigose hairs, average length of hairs on immature ray florets 1 mm, average length of hairs on involucral bracts: 0.15 cm, colored white on involucral bracts; NN155D, and immature ray florets; 150D, hairs on immature ray florets adpressed.

*Peduncle*.—Strong, straight on top of main flowering stem, average of 14.2 cm in length and 6.5 mm in diameter, color; 143A and 144B, surface moderately glossy and densely covered with short strigose hairs; an average of 2 mm in length and 156D in color.

*Ray florets*.—Average of 20 (varying between 18 and 22), rotate around the disc, oblong to elliptic in shape, average of 3.6 cm in length and 1.4 cm in width, emarginate to praemorse apex, cuneate base, entire margins, both surfaces are glabrous and velvety, densely covered with very short adpressed hairs, 0.5 mm in length and 12C in color, color; when opening upper surface 14A, lower half 17A, when opening lower surface 12A, margins 13A, when fully open upper surface 14A to 14B, lower half 21A, when fully open lower surface 17B, central section 15B.

*Disc florets*.—Average of 1,250, 25 whorls arranged spirally on a conical receptacle, lower 92.5% fused into tube, tubular, upright, about 8 mm in length and 3 mm in width, tubular, upper 7.5% free, free lobes have entire margins, apices of free lobes acute and curled backwards, both surfaces glabrous and slightly glossy, color; when opening upper and lower surface 200A, lower half 155C, when fully open upper and lower surface 203A.

Reproductive organs (present only on disc florets):

*Gynoecium*.—Pistil; 1, 6 mm in length, style; 3 mm in length, stigma; cleft, decurrent, 203A in color, 4.5 mm in diameter, ovary; N155C in color.

*Androecium*.—Stamens; 5, filaments; 3 mm in length, 155A in color, anther; narrow oblong in shape, 3 mm in length, 0.5 mm in width, 203A in color, pollen; moderate in quantity and 17A in color.

*Fruit/seed*.—None observed.

It is claimed:

1. A new and distinct cultivar of *Rudbeckia* plant named 'RUDBDIV658' substantially as herein illustrated and described.

* * * * *